United States Patent [19]

Frey

[11] 4,032,994
[45] July 5, 1977

[54] HIP JOINT PROSTHESIS

[75] Inventor: Otto Frey, Winterthur, Switzerland

[73] Assignee: Sulzer Brothers Limited, Winterthur, Switzerland

[22] Filed: May 24, 1976

[21] Appl. No.: 688,994

[30] Foreign Application Priority Data

June 3, 1975 Switzerland ............... 7113/75

[52] U.S. Cl. ............... 3/1.912; 128/92 C; 128/92 CA

[51] Int. Cl.² ................ A61F 1/24

[58] Field of Search ........ 3/1, 1.912, 1.913, 1.91; 128/92 C, 92 CA

[56] References Cited

UNITED STATES PATENTS 3,658,056  4/1972  Huggler et al. ............... 3/1.912

3,894,297  7/1975  Mittelmeier et al. ............... 3/1

FOREIGN PATENTS OR APPLICATIONS 2,139,878  2/1973  Germany ............... 3/1.912
2,059,381  3/1972  Germany ............... 3/1.913

Primary Examiner—Ronald L. Frinks
Attorney, Agent, or Firm—Kenyon & Kenyon, Reilly, Carr & Chapin

[57] ABSTRACT

The joint head is mounted via a sleeve of a cup-shaped member to rotate and move axially relatively to a pin on the prosthesis stem while at least one groove-like recess is formed between the sleeve and joint head to allow passage of lubricant. The movement of the joint head produces a "reciprocating pump" effect on the lubricating fluid.

9 Claims, 3 Drawing Figures

HIP JOINT PROSTHESIS

This invention relates to a hip joint prosthesis.

As is known, hip joint prostheses generally have a spherical joint head mounted on a pin so as to be movable axially and rotatably around the pin axis, the pin being rigidly secured to a stem for anchorage in the thigh bone. A prosthesis of this kind is known, e.g. from Swiss Patent Specification 490,077 and has the advantage that the joint head is movable on the pin as well as in an acetabulum. The lubrication of this prostehsis has been effected via a passage in the joint head as a result of a reciprocating-pump-like action of the pin in its axial reciprocations as the joint experiences loads and as loads are removed from the joint. However, practical experience gained with this prosthesis has shown that the lubrication of the pin bearings is sometimes inadequate.

Accordingly, it is an object of the invention to improve the lubrication of a hip joint prosthesis.

It is another object of the invention to provide a hip joint prosthesis which is able to effect lubrication of its components during use.

It is another object of the invention to improve the lubrication of a hip joint prosthesis in a simple manner.

Briefly, the invention provides a hip joint prosthesis which comprises a pin, a cup-shaped member and a spherical joint head with a means of communicating the pin surfaces with a reservoir of lubricant, i.e. synovia, outside the prosthesis. To this end, the cup-shaped member is rotatably and axially movably mounted on the pin and includes a metal sleeve which defines a bore surrounding the pin and an end wall facing an end of the pin. The sleeve also has an outer conical circumferential surface while the end wall has a passage therethrough communicating with the bore. The joint head is rigidly mounted on the sleeve and has a self-locking interior cone-shaped surface in engagement with the sleeve surface while being spaced from the end wall of the cup-shpaed member to define a chamber therebetween. This chamber is also in communication with the passage in the end wall.

The means of communicating the pin surfaces with a reservoir of lubricant includes at least one groove-like recess in the conical surface of the sleeve which communicates the exterior space around the sleeve and joint head with the chamber between the joint head and end wall of the cup-shaped member. Thus, lubricant is able to pass between the exterior space and the bore of the cup-shaped member via the recess, the chamber and the passage in the end wall of the cup-shaped member.

The prosthesis also includes a stem which is rigidly secured to the pin for anchoring the prosthesis in a thigh bone.

As in the known construction, the axial movement of the pin in the sleeve acts as a reciprocating pump which intakes synovia through the recesses in the conical surface of the sleeve into the internal chamber and passage of the joint head and cup-shaped member, then forces the synovia out of the spaces and passages again. Since considerably more synovia is available for intake in the region around a femur neck and metal sleeve than in the prior art acetabulum — which is usually a prosthesis too — the lubricating action for the pin bearing is improved considerably.

Another advantage of the construction is that the sleeve of the cup-shaped member and joint head can be made of various materials. The invention is therefore very advantageous for a prosthesis whose joint head is made of a biocermaic and whose sleeve is made of one of the metal alloys known for implants. If required, the pin and the intramedullary stem can also be made of metals which are a different alloy from the metal used for the sleeve.

In case the prosthesis is used with an artificial acetabulum, it is advantageous if a passage is formed in the joint head to extend from the chamber therein substantially radially and outwardly to the outer spherical surface of the joint head. In this case, it is then possible, contrary to the known construction, for lubricant to also pass through the joint head to arrive between the rubbing surfaces of the prosthetic acetabulum and the joint head.

These and other objects and advantages of the invention will become more apparent from the following detailed description and appended claims taken in conjunction with the accompanying drawings in which:

Figure 1:
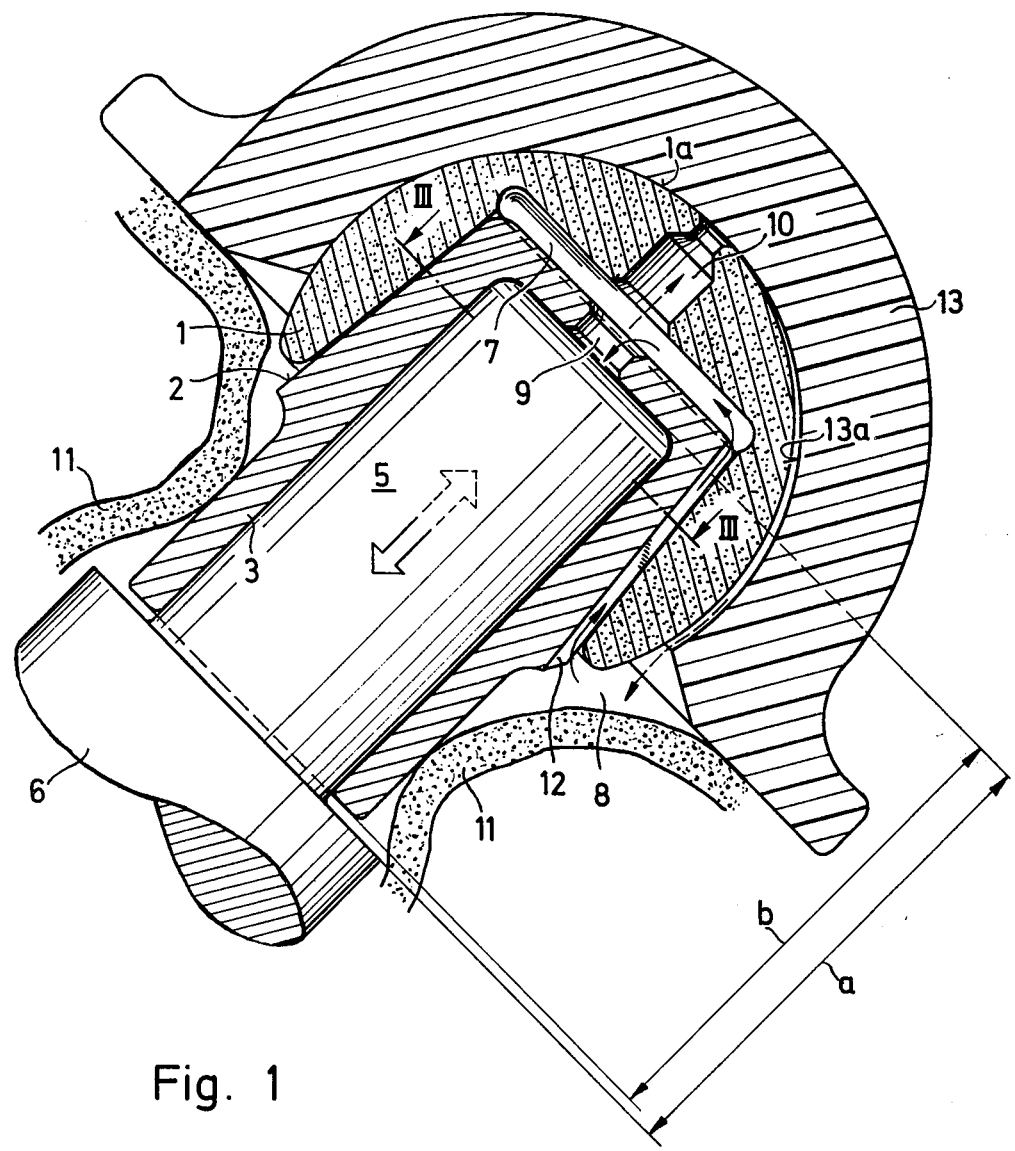
FIG. 1 illustrates a sectional view of a first embodiment of the invention in association with a prosthetic acetabulum.

Referring to FIG. 1, the hip joint prosthesis includes a joint head 1 made, e.g. of a bioceramic, this term denoting high-melting sintered aluminum oxide ($Al_2O_3$) ceramic having an $Al_2O_3$ content of at least 99.5%, a density of at least 3.90 g/cm³ and a grain size of less than 8 microns ($\mu$m). The joint head 1 includes a self-locking interior cone-shaped surface by which the head 1 is rigidly connected to a metal sleeve 3 of a cup-shaped member 2. Advantageously, the sleeve 3 as well as the remainder of the cup-shaped member is made of a CrNiMoCo (Chromium-Nickel-Molybdenum-Cobalt) alloy which is widely used for implants; however, the sleeve 3 can be made of some other metal, e.g. titanium, or of some other alloy, e.g. a titanium alloy. The outer circumferential surface of the sleeve 3 is also conical and is tapered in similar fashion to the interior of the joint head 1 with the taper being from 1:10 to 1:20. As shown, the joint head 1 is spaced from the end wall of the cup-shaped member to define a chamber 7 while a passage 9 is formed in the end wall in communication with the chamber 7.

The sleeve 3 of the cup-shaped member is, in turn, rotatably and axially movably mounted via a bore 4 on a metal pin 5 which merges by way of a flange-like or collar-like shoulder 6 of a stem (not further shown) for anchoring the prosthesis in a thigh bone. The axial length $a$ of the pin 5 and the axial length $b$ of the sleeve 3 are so adapted to one another that when a load is applied to the joint, the end wall of the cup-shaped member abuts the pin end face, i.e. the sleeve 3 does not bear on the shoulder 6.

Figure 3:
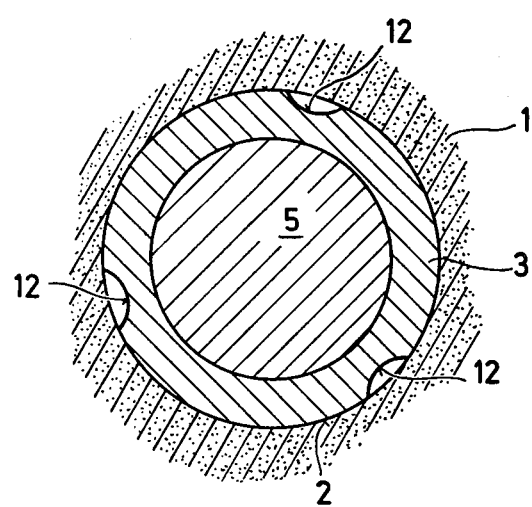
FIG. 3 illustrates a view taken on line III—III of FIGS. 1 and 2.

The sleeve 3 is provided with at least one uninterrupted groove-like recess 12 which communicates the chamber 7 within the joint head 1 with the exterior space 8 in the tissue around the sleeve 3 and joint head 1. As shown in FIG. 3, these groove-like recesses 12 are distributed uniformly around the periphery of the sleeve 3. The space 8 is substantially sealed off from the surrounding area by the post-implantation invasion of scar tissue 11 shown diagrammatically in FIG. 1 and is full of synovia. Thus, this reservoir of lubricant, i.e. synovia, communicates via the recesses 12 and the chamber 7 between the joint head 1 and the member 2 with the bore 4 of the sleeve 3.

In the example shown in FIG. 1, the joint head 1 is received in a prosthetic acetabulum 13 made, e.g. of high-molecular hard polyethylene. Thus, the joint head 1 is also formed with a passage 10 via which the inner chamber 7 communicates with the outer spherical surface of the joint head 1, i.e. with the space 13a between the head 1 and the acetabulum 13.

Figure 2:
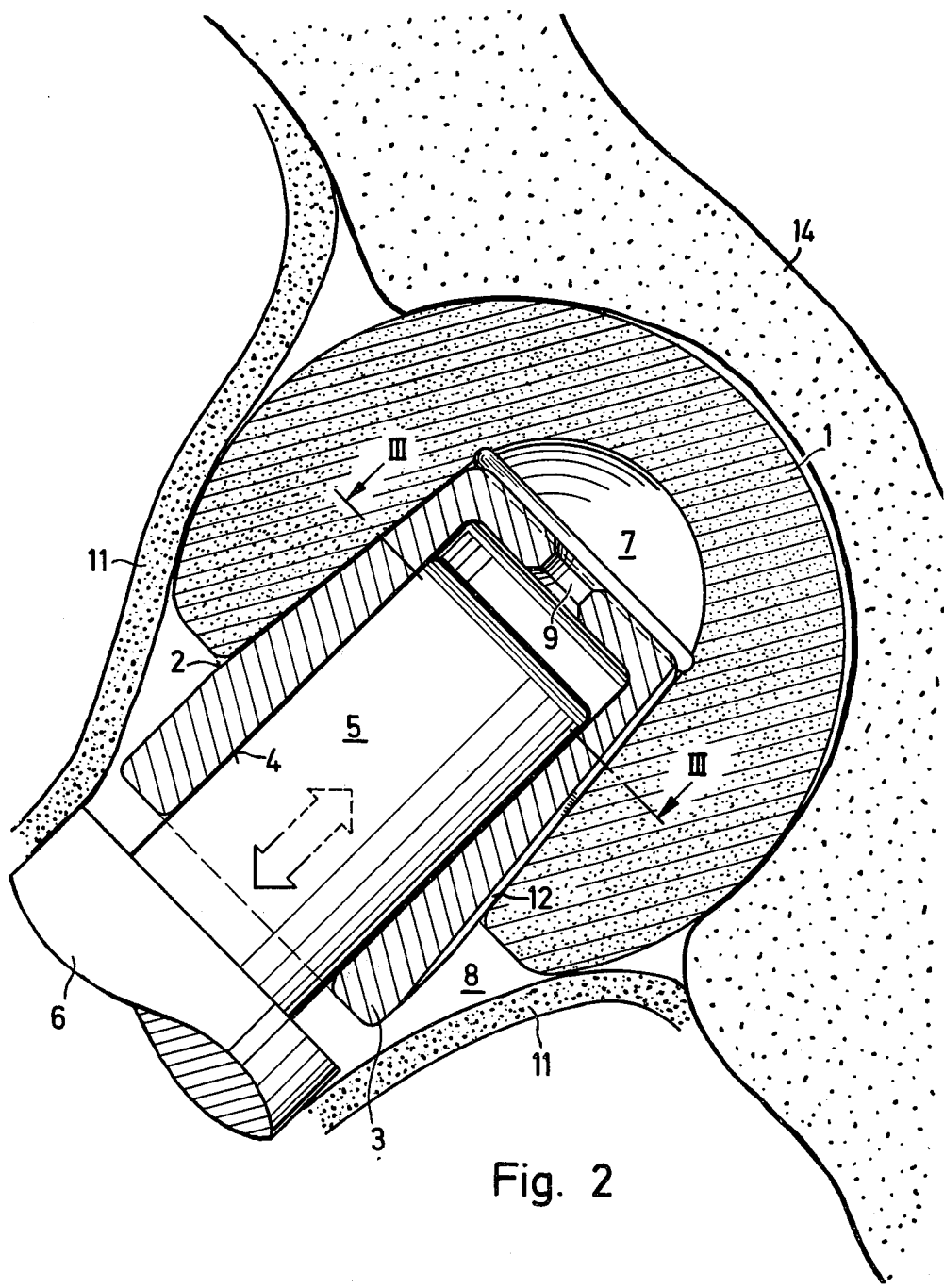
FIG. 2 illustrates a similar view to FIG. 1 of a second embodiment in which the joint head cooperates directly with the natural acetabulum in a hip bone.

Referring to FIG. 2, wherein like reference characters indicate like parts as above, the prosthesis may also be fitted directly in the natural acetabulum in a hip bone 14 and is therefore devoid of the passage 10 (FIG. 1) in the joint head 1.

As in the known construction, during use, the pin 5 reciprocates axially in the sleeve 3 as loads are applied to and removed from the joint and cooperates with the sleeve 3 to form a kind of reciprocating pump which first intakes synovia from the space 8 through the recess 12 into the chamber 7 and then through the passage 9 into the bore 4; the synovia being forced back into the space 8 when the joint is loaded. Intensive lubrication of the pin 5 moving in the bore 4 is therefore provided since, in contrast to the earlier construction, the intake route is devoid of a narrow gap between the acetabulum 13 and the joint head 1.

Simultanously as the joint of FIG. 1 is loaded, some of the liquid displaced by means of the "reciprocating pump" if forced through the passage 10 to arrive between the rubbing surfaces of the joint head 1 and acetabulum 13, so that lubrication of movements of the surface in the acetabulum 13 are also improved.

What is claimed is:

1. A hip joint prosthesis comprising
   a pin;
   a stem rigidly secured to said pin for anchoring in a thigh bone;
   a cup-shaped member rotatably and axially movably mounted on said pin, said member having a sleeve defining a bore surrounding said pin and an end wall facing an end of said pin, said sleeve having an outer conical circumferential surface and said end wall having a passage therethrough communicating with said bore;
   a spherical joint head rigidly mounted on said sleeve, said joint head having a self-locking interior cone-shaped surface in engagement with sleeve surface and being spaced from said end wall to define a chamber therebetween, said chamber being in communication with said passage in said end wall; and
   at least one groove-like recess in said conical circumferential surface of said sleeve communicating the exterior space around said sleeve and joint head with said chamber.

2. A prosthesis as set forth in claim 1 wherein said joint head includes a passage extending from said chamber radially outwardly to the outer surface of said joint head.

3. A prosthesis as set forth in claim 1 wherein said cup-shaped member is made of metal.

4. A prosthesis as set forth in claim 3 wherein said joint head is made of a bioceramic.

5. A prosthesis as set forth in claim 1 wherein said stem includes a shoulder facing said sleeve, said shoulder being in spaced relation to said sleeve when said end wall abuts said pin.

6. In combination with the hip prosthesis of claim 1, a prosthetic acetabulum having a spherical surface receiving said joint head.

7. The combination as set forth in claim 6 wherein said joint head includes a passage extending from said chamber radially outwardly to the outer surface of said joint head.

8. A hip joint prosthesis comprising
   a pin;
   a cup-shaped member rotatably and axially movably mounted on said pin, said member having a sleeve defining a bore surrounding said pin and an end wall facing an end of said pin, said sleeve having an outer conical circumferential surface and said end wall having a passage therethrough communicating with said bore;
   a spherical joint head rigidly mounted on said sleeve, said joint head having an interior cone-shaped surface in engagement with said sleeve surface and being spaced from said end wall to define a chamber therebetween, said chamber being in communication with said passage in said end wall; and
   at least one groove-like recess in said conical circumferential surface of said sleeve communicating the exterior space around said sleeve and joint head with said chamber.

9. A hip joint prosthesis comprising
   a metal pin;
   a stem rigidly secured to said pin for anchoring in a thigh bone;
   a metal cup-shaped member rotatably and axially movably mounted on said pin, said member having a sleeve defining a bore surrounding said pin and an end wall facing an end of said pin, said sleeve having an outer conical circumferential surface and said end wall having a passage therethrough communicating with said bore;
   a bioceramic sperical joint head rigidly mounted on said sleeve, said joint head having a self-locking interior cone-shaped surface in engagement with said sleeve surface and being shaped from said end wall to define a chamber therebetween, said chamber being in communication with said passage in said end wall; and
   a plurality of uninterrupted groove-like recesses in said conical circumferential surface of said sleeve communicating the exterior space around said sleeve and joint head with said chamber to intake synovia from the exterior space into said chamber to form a reservoir of synovia therein.

* * * * *